US00PP10894P

United States Patent [19]

Strode

[11] Patent Number: Plant 10,894

[45] Date of Patent: May 11, 1999

[54] SPATHIPHYLLUM PLANT NAMED '61352'

[75] Inventor: Randall E. Strode, Apopka, Fla.

[73] Assignee: Agri-Starts, Inc., Apopka, Fla.

[21] Appl. No.: 08/863,466

[22] Filed: May 27, 1997

[51] Int. Cl.[6] ..... A01H 5/00

[52] U.S. Cl. ..... Plt./364

[58] Field of Search ..... Plt./88.1, 364

[56] References Cited

U.S. PATENT DOCUMENTS

P.P. 8,844 7/1994 Van Dordrecht ..... Plt./88.1

*Primary Examiner*—Howard J. Locker

*Attorney, Agent, or Firm*—James A. Lucas

[57] ABSTRACT

A new and distinct variety of Spathiphyllum plant characterized particularly as to novelty by demonstrating a greater suckering propensity than its parents at the juvenile stage, and producing more and shorter blooms and having shiny, dark green leaves without the burn problems of the pollen parent.

1 Drawing Sheet

BACKGROUND OF THE DISCLOSURE

This invention relates to a new and distinct plant variety of the Araceae family and, specifically, to a new and distinct plant variety of Spathiphyllum which is named *Araceae Spathiphyllum* '61352'.

Certain plant varieties of the Araceae family are well known in the foliage plant market and among these is the 'Petite' variety of Spathiphyllum. This variety is characterized by, among other things, sporting more and shorter blooms and dark green leaves without the burn problems associated with 'Petite'.

The variety forming the subject matter of this application is hybrid of interspecific genetic background from a cross between 'Annette' (unpatented) and 'Petite' (unpatented). A general objective of the invention has been to provide a variety of the Spathiphyllum species which would be distinguishable from the other known varieties of this plant and suitable for sale in the foliage plant marketplace.

This new variety of Spathiphyllum was asexually reproduced by tissue culture near Apopka, Fla. and such reproduction has shown this new variety to come true in successive generations. This propagation of the new variety by tissue culture in the usual controlled environment clearly shows the continued maintenance of the characteristics described herein which distinguish this new variety from the parent varieties and all other known and related varieties mainly by more and shorter blooms and darker green leaves. In addition, it is resistant to the burn problems associated with 'Petite'. The propensity to form suckers and a proliferation of dark foliage results in an early finished density and an attractive specimen distinguishing it from its parents and from other varieties. The length of the peduncles is about 30% less than that of the parents, thus serving to contribute to a compact size thereby facilitating the packaging for shipment of the plant.

BRIEF DESCRIPTION OF THE PHOTOGRAPH

The accompanying color photographic illustration shows, as nearly true as it is reasonably possible in a color illustration of this character, the whole plant grown in a pot.

BOTANICAL DESCRIPTION OF THE PLANT

All color references below are measured against The Royal Horticultural Society Colour Chart. Colors are as true as is reasonably possible to attain in color illustrations of this type. The cultivar may vary somewhat in phenotype depending upon horticultural practices such as light level and fertilization rate, without, howerver any change in genotype.

Parentage:

*Seed parent.*—Spathiphyllum 'Annette'.

*Pollen parent.*—Spathiphyllum 'Petite'.

Plant:

*Form.*—Bush.

*Growth.*—Vigorous; matures in 7 to 9 months. Average height of specimen grown to maturity is 18" to 24" in a 6" pot.

*Spread of mature specimen.*—24" in a 6" pot.

*Time from liner to market size.*—7–9 months.

*Suckering.*—Specimen suckers 50% more than its parents while in juvenile stage (within 8 weeks).

Foliage:

*Mature foliage color.*—137A Green.

*Size of fully developed leaf.*—Small, 1.2"–2.4" wide; 5.6"–6.8" long as measured from point of attachment to tip.

*Quantity.*—Abundant.

*Pose at maturity.*—Ascending.

*New foliage color.*—Upper side 143A Green; Under side 137D Green.

*Shape.*—Lanceolate.

*Texture.*—Smooth with gentle corrugation of the surface area between the ribs of venation.

*Ribs and veins.*—Depressed on top surface; same color as leaf blade.

*Edge.*—Smooth.

*Under side.*—Smooth.

*Glossiness.*—20% more gloss than other varieties.

*Stipules.*—None.

*Resistance to disease.*—Average for the species in this market class.

*Petiole.*—Length — 6"; Width — ¼–½" base. Color — 137B (dark green).

*Geniculum.*—Length 1½"; forms a 10% angle; same color as leaf blade, 137B.

INFLORESCENCE

Blooming habit:

*Blooms.*—Profusely.

*Recurrent.*—Spring and Fall. Will bloom in 9–11 weeks when treated with gibberellic acid.

Bud:

*Color.*—155A White.

*Size.*—Medium; 3.2"–3.6" long.

Peduncle:

*Length.*—13–16 inches; nested in foliage.

*Aspect.*—Smooth.

*Strength.*—Erect and slender.

*Attitude (relative to spathe).*—Upright.

*Coloration.*—137B green.

Spathe:

*Size.*—Medium and 1.6"–2" wide, 3.6"–4" long when fully expanded.

*Stems.*—30% shorter than most varieties.

*Color.*—155D White; turns green after 21–30 days.

*Texture.*—Thick, leathery, and not affected by wet or hot weather.

*Appearance.*—Inside and outside are satiny.

*Form.*—Oval and pointed.

*Attitude.*—Upright, parallel relative to spadix.

*Apex.*—Typical for the species. Length is twice the width.

*Symmetry.*—Uniform.

*Margin characteristics.*—Smooth.

*Length.*—3½".

*Width.*—2".

*Arrangement.*—Single spadix.

*Persistence.*—Stays on and dries from white to green. No fragrance.

*Lastingness.*—On the plant — Three weeks. As cut flower — Two weeks.

Spadix:

*Size.*—Small.

*Color.*—Male 155A White; Female 158B White.

*Length.*—1½".

*Width.*—½".

Reproductive organs:

*Perianth.*—Shape size and white color not unlike those of the genus per se.

*Corolla.*—White and minute; typical of the genus.

*Androecium.*—Filaments white; not normally easily visible until pollen release. Size and character are within the normal range for the genus; Anthers and pollen are white.

*Gynoecium.*—Color is white; stigma is exposed after exposure of spadix; minute and not readily discernible without magnification. Pollen — Color 155D White; Styles — Columnar, even, heavy, and short in length. Ovaries are white, and are enclosed in calyx; They are not readily visible without magnification and dissection of the flower.

Fruit:

*Variety.*—Fertile.

*Form.*—Seeds protruding.

I claim:

1. A new and distinct variety of Spathiphyllum plant as herein shown and described, characterized particularly as to novelty by demonstrating a greater suckering propensity than its parents, producing more and shorter blooms, and having glossy, dark green leaves without the burn problems associated with the pollen parent.

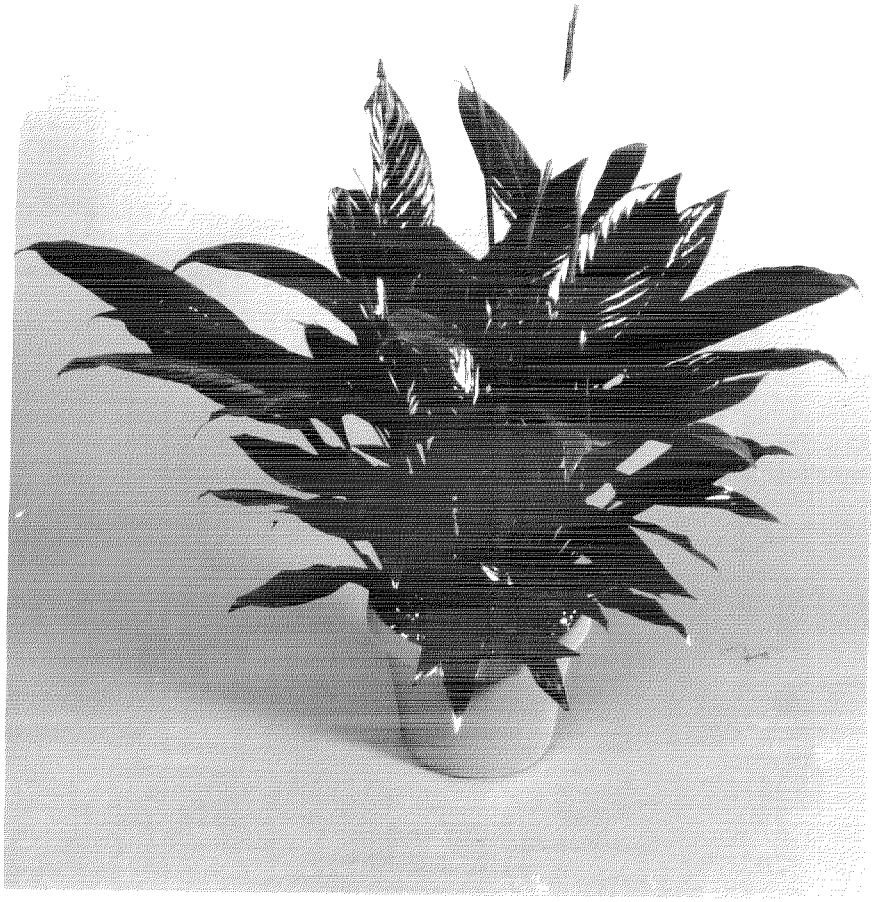

* * * * *